(12) United States Patent
Gradon et al.

(10) Patent No.: US 6,272,933 B1
(45) Date of Patent: Aug. 14, 2001

(54) RESPIRATORY HUMIDIFICATION SYSTEM

(75) Inventors: Lewis George Gradon; Stephen William McPhee; Paul John Seakins; Peter John Leonard, all of Auckland (NZ)

(73) Assignee: Fisher & Paykel Limited (NZ)

( * ) Notice: Subject to any disclaimer, the term of this patent is extended or adjusted under 35 U.S.C. 154(b) by 0 days.

(21) Appl. No.: 09/457,797

(22) Filed: Dec. 9, 1999

Related U.S. Application Data

(62) Division of application No. 09/097,832, filed on Jun. 16, 1998.

(51) Int. Cl.[7] .............................. G01F 1/00; G01F 1/86; G01F 15/02; A61M 15/00; F23D 11/00
(52) U.S. Cl. .................... 73/861; 73/861.01; 73/861.02; 73/861.03; 73/866.5; 128/203.16; 128/203.17; 128/203.26; 128/203.27
(58) Field of Search .................. 73/861, 861.01, 73/861.02, 861.03, 866.5; 128/203.16, 203.17, 203.26, 203.27

(56) References Cited

U.S. PATENT DOCUMENTS

| | | |
|---|---|---|
| 4,098,853 | 7/1978 | Brown et al. . |
| 4,393,013 | 7/1983 | McMenamin . |
| 4,436,674 | 3/1984 | McMenamin . |
| 4,589,409 | 5/1986 | Charburn et al. . |
| 4,621,632 | 11/1986 | Bartels et al. . |
| 4,705,936 | 11/1987 | Fowler . |
| 4,708,831 | 11/1987 | Elsworth et al. . |
| 4,921,642 | 5/1990 | LaTorraca . |
| 5,558,084 | 9/1996 | Daniell et al. . |

Primary Examiner—Hezron Williams
Assistant Examiner—Dennis Loo
(74) Attorney, Agent, or Firm—Trexler, Bushnell, Giangiorgi, Blackstone & Marr, Ltd.

(57) ABSTRACT

A flow probe for use in a humidification system is disclosed. The flow probe is adapted to be positioned in a humidified gases flow (for example oxygen or anesthetic gases) such as that which is provided to a patient in a hospital environment. The flow probe is designed to provide both temperature and flow rate sensing of the gases flow by incorporating two sensors (preferably thermistors) and the shape and alignment of the probe enables accurate readings by reducing the occurrence of condensation on the sensors. A number of possible applications are disclosed wherein the flow sensor is included in humidification control systems which provide a patient with a desired humidity level or simplify the amount of user input required or wherein the flow sensor provides a controller with flow information which may then be used to determine certain, possibly dangerous, conditions (such as incorrect flow sensor placement, breathing circuit disconnected, no water in the humidification chamber or humidity out of required limits).

12 Claims, 6 Drawing Sheets

RESPIRATORY HUMIDIFICATION SYSTEM

This is a divisional of copending application Ser. No. 09/097,832 filed on Jun. 16, 1998.

BACKGROUND OF THE INVENTION

1. Field of the Invention

This invention relates to gases distribution systems and in particular, though not solely, to respiratory humidifier systems which humidify gases for a patient, or other person in need of such gases, to breathe.

2. Description of the Prior Art

Many, if not all, existing respiratory humidification systems which deliver humidified gases (such as oxygen or anaesthetic gases) to a patient, or other person in need of such gases, operate as temperature controllers. That is, the temperature of the gases leaving the humidification device in the breathing circuit is monitored and the heat source controlled in response to changes in that temperature to achieve a desired outgoing humidified gases temperature. An example of this type of humidifier control system is disclosed in our prior U.S. Pat. No. 5,558,084. This method of control has a number of disadvantages including:

- In situations with high incoming gases temperature (approaching the desired outgoing gases temperature) little heat is necessarily supplied to the gases by the humidification process to achieve the required temperature. Accordingly, little humidification of the gases is also achieved.
- The dependency on temperature sensors in this control method means that incorrect placement or connection of the temperature sensors can lead to impaired performance of the entire humidification and breathing system.
- Lack of flow sensors which, if provided, would enable certain breathing circuit conditions to be easily recognised and appropriate action to be taken by the humidification device (and/or the gases supply). Flow sensors have previously not been utilised in humidification systems due to insufficient robustness and problems of condensation occurring on the flow sensor, leading to incorrect flow readings.
- Gases being supplied to the patient at a pressure/humidity combination which is inappropriate. It is well known that certain humidity levels are required of gases which are to be administered to a patient. Different humidity values are specifically suitable to intact (for example face mask) or bypassed (intubation delivery of gases) airways. Temperature sensing alone can not ensure that these required temperature/humidity values are achieved.
- Some existing respiratory humidification devices require users to adjust dials which have little or no intuitive relationship to the actual physical parameters they are intended to control. Often the dials adjust the required gases outlet temperature and/or the heating supplied by the heater wire provided within the conduit connecting humidifier to patient (and sometimes also the conduit connecting the patient back to the gases supply). The most important parameter in humidified gases supply to a patient is the humidity of the gases as insufficient humidity can very quickly dehydrate the patient's airways. Accordingly, users have little or no idea where to position the dials to produce the desires result of optimum humidity in the supplied gases at the existing flow rate. An automated system in which the user need only inform the humidification device if the patient receiving the humidified gases has intact or by-passed airways would be a major advance.
- Many existing respiratory humidification devices display the gases temperature being supplied to the patient. As previously mentioned, the most important parameter in respiratory humidification systems is the humidity of the gases. Often, the temperature displayed has no relationship to the actual humidity of the gases being supplied to the patient due to heating in the delivery circuit and can therefore be misleading to the average health care professional. It would, therefore, be an advantage if the temperature displayed was in some way related to or indicative of the humidity of the gases being supplied to the patient.

BRIEF SUMMARY OF THE INVENTION

It is, therefore, an object of the present invention to provide a respiratory humidifier system which will go at least some way towards overcoming the above disadvantages or which at least provide the industry with a useful choice.

Accordingly, in a first aspect, the invention consists in sensor probe means adapted for positioning in a flow of humidified gases comprising:

- sensor housing means adapted for positioning in said gases flow, said sensor housing means having a longitudinal axis substantially perpendicular to said humidified gases flow and a sensing end,
- sensing means housed within said sensor housing means at or near said sensing end, and
- at least one projecting tab means extending laterally from said sensor housing means, said at least one projecting tab means providing surfaces which enable liquid condensate to disperse away from said sensing end of said sensor housing means.

In a second aspect, the invention consists in humidification apparatus for humidifying a gases flow to be supplied to a patient or other person in need of such gases comprising:

- humidification chamber means adapted to hold a quantity of water and having an inlet and an outlet to allow said gases flow to pass through said humidification chamber means,
- heating means provided adjacent said humidification chamber means and adapted to provide heat to said quantity of water in said humidification chamber means in order to provide water vapour to said gases flow passing through said humidification chamber means,
- gases transportation pathway means connected to said outlet of said humidification chamber means to convey said gases flow to said patient or other person in need of such gases,
- flow probe means adapted to sense the flow rate of said gases flow,
- temperature sensing means adapted to sense the temperature of said gases flow,
- user input means to allow a user to set a required temperature of said gases flow,
- control means which receives input from said flow probe means, said temperature sensing means and said user input means and control said heating means in response to said inputs to maintain said gases flow at said required temperature.

In a third aspect, the invention consists in humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, said heating means utilising a measurable quantity of power, gases transportation pathway means connected to said outlet of said humidification chamber means to convey said gases flow to said patient or other person in need of such gases, flow probe means adapted to sense the flow rate of said gases flow, control means which receives input from said flow probe means and storing a program which causes the control means to:
i) calculate the power usage required of said heating means in order to humidify said gases flow to a predetermined level at the gases flow rate sensed by said flow probe means,
ii) determine the power presently being utilised by said heating means, and
iii) supply said predetermined level of power to said heating means if the determined present power utilisation of said heating means is less than said required power usage.

In a fourth aspect, the invention consists in humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, gases transportation pathway means connected to said outlet of said humidification chamber means to convey said gases flow to said patient or other person in need of such gases, flow probe means adapted to sense the flow rate of said gases flow, temperature sensing means adapted to sense the temperature of said gases flow, user input means to allow a user to select a desired gases humidity level of said gases flow, data storage means containing information on target gases temperatures at various gases flow rates for a number of humidification chamber outlet means temperatures, control means which receives input from said temperature sensing means and said user input means and using said flow information from said flow probe means repeatedly obtains corresponding target temperature information from said data storage means corresponding to the desired gases humidity level and varies the heat provided by said heating means until the sensed temperature is substantially equivalent to said target temperature in order to obtain said desired gases humidity level.

In a fifth aspect, the invention consists in humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, gases transportation pathway means connected to said outlet of said humidification chamber means to convey said gases flow to said patient or other person in need of such gases, flow probe means adapted to sense the flow rate of said gases flow, temperature sensing means adapted to sense the temperature of said gases flow, user input means which may be in one of a predetermined number of states corresponding to one of a number of gases delivery configurations, each configuration optimally requiring a predetermined gases temperature and humidity level, control means which receives input from said flow probe means, said temperature sensing means and said user input means and controls said heating means to provide said gases flow to said patient or other person in need of such gases at a temperature and humidity level as indicated by said user input means.

In a sixth aspect, the invention consists in humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, gases transportation pathway means connected to said outlet of said humidification chamber means to convey said gases flow to said patient or other person in need of such gases, said gases transportation pathway means having a patient end, distal to said end connected to said outlet of said humidification chamber means, first temperature sensing means adapted to sense the temperature of said gases flow substantially at said outlet of said humidification chamber means, second temperature sensing means adapted to sense the temperature of said gases flow substantially at said patient end of said gases transportation pathway means, display means adapted to display temperature information to a user, control means which receives input from said first temperature sensing means and outputs a signal to said display means to cause a temperature to be displayed to the user which is the lower of the temperatures sensed by said first and said second temperature sensing means.

In a seventh aspect, the invention consists in humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, gases transportation pathway means connected to said outlet of said humidification chamber means to convey said gases flow to said patient or other person in need of such gases, flow probe means adapted to sense the flow rate of said gases flow, and control means which receives input from said flow probe means and compares the sensed flow rate of said gases flow with a predetermined minimum required gases flow rate and places the humidification apparatus into a safe mode of operation if the sensed rate is less than said predetermined minimum rate.

In an eighth aspect the invention consists in humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, gases transportation pathway means connected to said outlet of said humidification chamber means to convey said gases flow to said patient or other person in need of such gases, said gases transportation pathway means having a patient end, distal to said end connected to said outlet of said humidification chamber means, humidity sensing means which senses the humidity of said gases flow being supplied to said patient, timer means which may be used to time certain humidification apparatus events, alarm means which may be energised to provide a warning signal after a predetermined alarm time, storage means which stores said alarm times for a number of associated sensed humidity values, and control means which stores a program which causes the control means to:
  i) receive input of said sensed humidity value from said humidity sensing means,
  ii) obtain from said storage means the alarm time associated with said sensed humidity value,
  iii) start said timer means,
  iv) wait until the time elapsed by said timer means substantially equals said alarm time and
  v) energise said alarm means to provide said warning signal.

In a ninth aspect the invention consists in humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, heating means power utilisation sensing means which monitors the level of power being used by said heating means, heating means temperature sensing means which senses the temperature of said heating means, gases transportation pathway means connected to said outlet of said humidification chamber means to convey said gases flow to said patient or other person in need of such gases, said gases transportation pathway means having a patient end, distal to said end connected to said outlet of said humidification chamber means, alarm means which may be energised to provide a warning signal after a predetermined alarm time, and control means which stores a program which causes the control means to:
  i) determine a difference temperature by subtracting the gases temperature determined by said gases flow temperature sensing means from the heating means temperature sensed by said heating means temperature sensing means,
  ii) determine a power requirement value for the heating means from said heating means power utilisation sensing means,
  iii) calculate a thermal conductivity value by dividing said power requirement value by said difference temperature,
  iv) energise said alarm means if said calculated thermal conductivity value is less than a predetermined minimum allowable thermal conductivity value.

In a tenth aspect the invention consists in humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, said heating means utilising a measurable quantity of power, gases transportation pathway means connected to said outlet of said humidification chamber means to convey said gases flow to said patient or other person in need of such gases, gases transportation pathway heating means which are energisable to supply heat to said gases flow along at least a part of the length of said gases transportation pathway means, gases temperature sensing means which senses the temperature of said gases flow leaving said humidification chamber means, user input means to allow a user to enter a required temperature offset value which is the required difference in temperature between the said sensed gases temperature and the temperature of the gases flow delivered to said patient, control means which stores a program which causes the control means to:
  i) determine the gases temperature of the gases leaving said humidification chamber means using said gases temperature sensing means,
  ii) receive said offset temperature value from said user input means, iii) calculate an airway set-point temperature by adding said gases temperature to said offset temperature, iv) energise said gases transportation pathway heating means to increase the temperature of said gases flow by said offset value along the length of said gases transportation pathway means.

To those skilled in the art to which the invention relates, many changes in construction and wisely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

The invention consists in the foregoing and also envisages constructions of which the following gives examples only.

One preferred form of the present invention will now be described with reference to the accompanying drawings in which.

DETAILED DESCRIPTION OF THE PREFERRED EMBODIMENT

Figure 5:
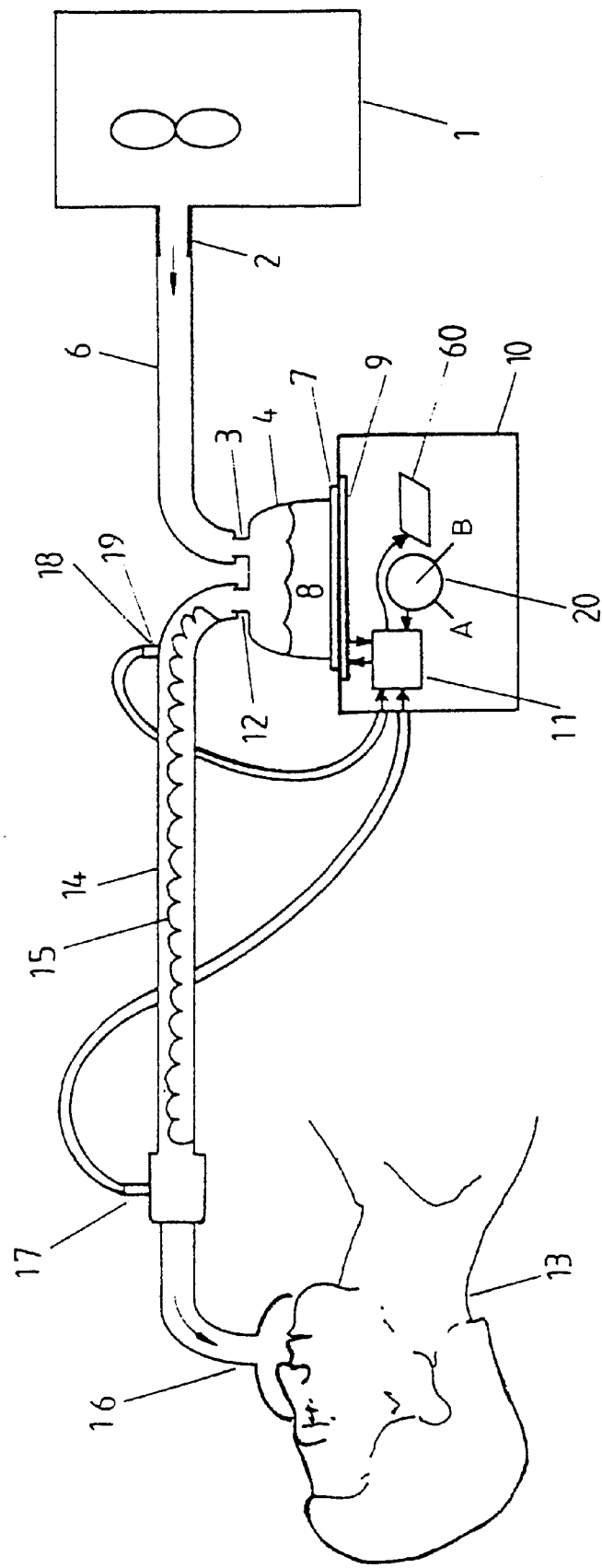
FIG. 5 is a schematic diagram of a respiratory humidification system incorporating the flow probe of FIG. 1.

With reference to the accompanying drawings and in particular to FIG. 5, an example humidification apparatus or respiratory humidification system incorporating preferred embodiments of the present invention is illustrated. Included in the respiratory humidification system is a ventilator or gases supply means or blower 1 having an outlet 2 which supplies gases (for example oxygen, anaesthetic gases or air) to the inlet 3 of a humidification chamber means 4 via a conduit 6. Humidification chamber means 4 may, for example comprise a plastics formed chamber having a metal base 7 sealed thereto. Humidification chamber 4 is adapted to hold a volume of water 8 which is heated by a heater plate means 9 under the control of controller or control means 11 of a humidification device or humidifier 10.

As the water within chamber 4 is heated it will slowly evaporate, mixing water vapour with the gases flow through the humidification chamber from ventilator 1. Accordingly, humidified gases leave humidification chamber 4 via outlet 12 and are passed to a patient or other person in need of such gases 13 through a gases transportation pathway or inspiratory conduit 14. In order to reduce condensation within the inspiratory conduit 14 and to raise the temperature of the gases provided to the patient 13 a heating wire means 15 may be provided which may be energised under the control of control means 11.

Figure 1:
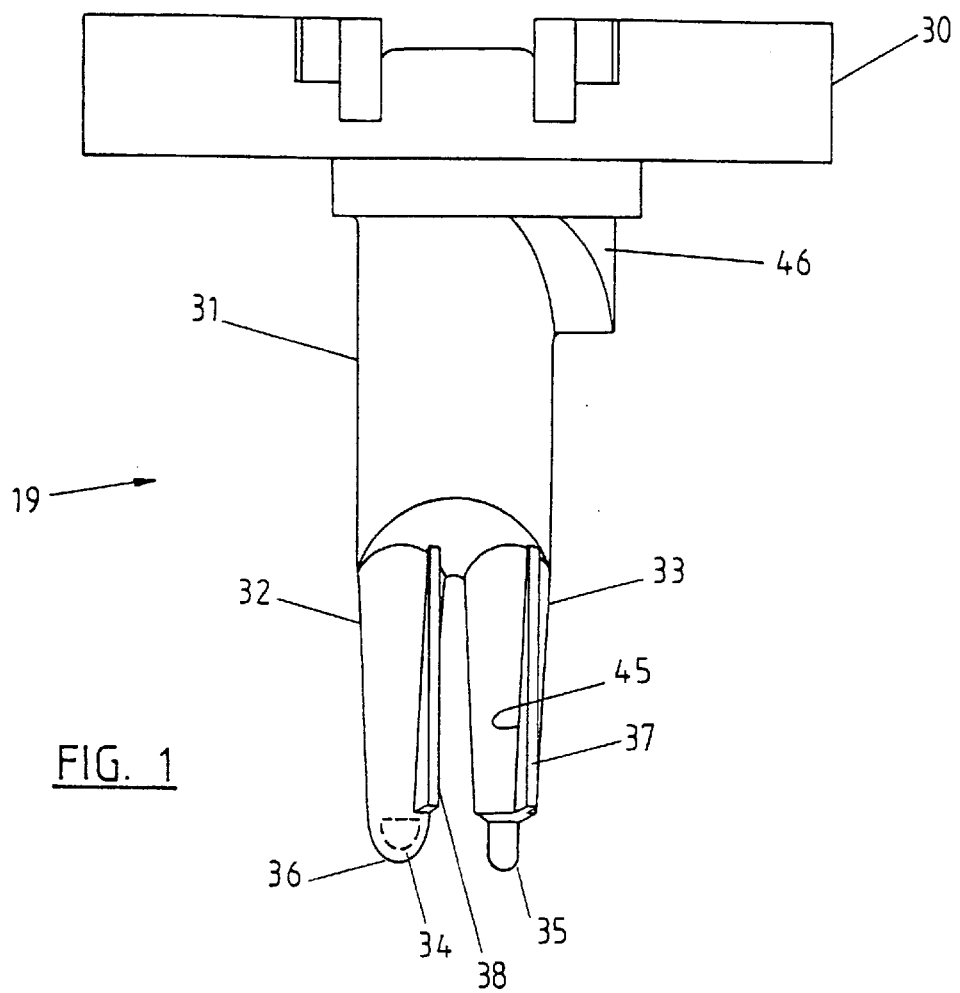
FIG. 1 is a front elevation of a flow probe constructed according to one preferred embodiment of the present invention.

In FIG. 1 a gases mask 16 is shown over the patient's nose and mouth (referred to as "Intact Airways" gases delivery) however it should be understood that many gases delivery configurations exist such as intubation in which a delivery tube is positioned in the patient's trachea to by-pass the patient's airways (known as "Intubated Airways" gases delivery). It is also possible to provide a return path for the patient's exhaled gases back to ventilator 1. In this case a suitable fitting such as a "Y-piece" may be attached between the patient (13), inspiratory conduit (14) and an expiratory conduit (not shown) which is connected to an inlet (not shown) of ventilator 1.

Control means 11 may for example comprise a microprocessor or logic circuit with associated memory or storage means which holds a software program which, when executed by control means 11, controls the operation of the humidification system in accordance with instructions set in the software and also in response to external inputs. For example, control means 11 may be provided with input from heater plate 9 so that control means 11 is provided with information on the temperature and/or power usage of the heater plate 9. In addition, control means 11 could be provided with inputs of temperature of the gases flow, for example a temperature sensing means or temperature probe 17 may be provided at or near the patient to indicate the gases temperature being received by the patient and a further temperature probe 18 may be provided to indicate to control means 11 the temperature of the humidified gases flow as it leaves outlet 12 of humidification chamber 4. Furthermore, a flow sensing means or flow probe 19 may be provided anywhere in the breathing circuit ("the breathing circuit" comprises the parts of the humidification apparatus through which the gases flow passes). The flow probe 19 is shown in FIG. 5 in the same position as temperature probe 18 as the two devices may both be provided in one probe as will described below.

A still further input to control means 11 may be a user input means or switch 20 which could be used to allow a user (such as a health care professional or the patient themselves) to set a desired gases temperature of gases to be delivered or a desired gases humidity level to be delivered or alternatively other functions could be controlled by switch 20 such as control of the heating delivered by heater wire 15 or selecting from a number of automatic gases delivery configurations (which will be described below).

A number of preferred embodiments of the system (or parts thereof) set out above will now be described in more detail.

Flow Probe

Figure 2:
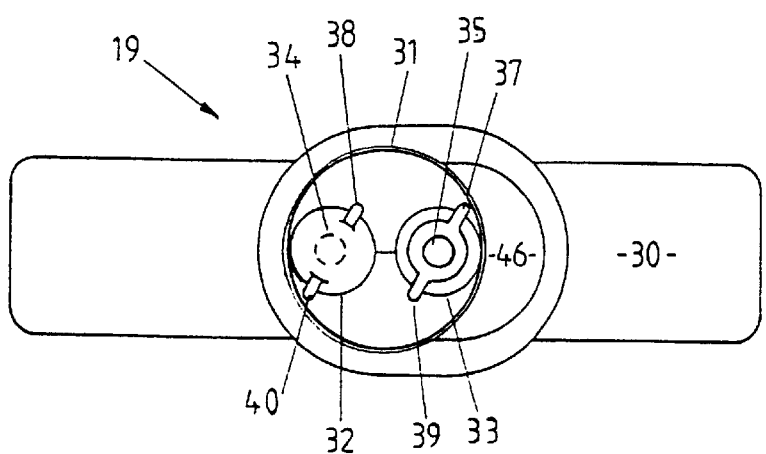
FIG. 2 is a view from below of the flow probe of FIG. 1.

With reference to FIGS. 1 and 2, the preferred form of flow probe 19 is shown. Flow probe 19 is preferably formed by moulding in a plastics material such as polycarbonate and comprises a base portion 30 adapted to hold wire conductors (48 in FIGS. 3 and 4) which carry electrical signals to and from control means 11. Protruding from base 30 is a stem 31 which has at least one sensor housing means 32 and 33 protruding from its end furthest from base 30. Sensor housing means 32 and 33 are preferably rounded in cross-section and substantially tapered or conical in elevation with a rounded tip at the end (the sensing end 36) furthest from base 30.

Shown in FIG. 1 are two sensor housing means 32 and 33. In the embodiment shown, one sensor housing means 32 is provided as a temperature sensing means while the other sensor housing means is provided to perform the function of flow rate sensing means. Within sensor housing means 32 and 33 are sensing means 34 and 35, for example thermistors (temperature dependent resistors), which are provided to sense the respective properties of temperature and flow rate of the gases flowing in the humidification system. In the case of the temperature sensing means 34, controller 11 may provide a voltage across the thermistor and receive a temperature signal in the form of the current passing through the thermistor which will be dependent on the temperature of the gases. To protect thermistor 34, sensor housing means 32 completely encases or encapsulates the thermistor, however as there is only a thin layer of plastics material between the thermistor and the gases flow, the temperature reading obtained is still accurate.

In the case of the flow sensing means 35, controller 11 may on occasion provide a current to the thermistor for a duration sufficient to warm the thermistor to a first known temperature and then disconnect the current supply and monitor the change in temperature of the thermistor (by monitoring its change in resistance). Controller 11 may then start a timing means and determine the length of time taken for the thermistor's temperature to drop to a second predetermined temperature. The time taken for the thermistor 35 to change in temperature from the first to the second known temperature along with a known cross-sectional area of gases flow (for example a 12 mm diameter conduit) providing controller 11 with an indication of the flow rate of the gases as they conduct heat away from the heated thermistor. It can be seen that thermistor 35 is not encased or encapsulated in the same way as thermistor 34. This is because any layer of material between the thermistor 35 and the gases flow would influence the heat transfer rate from thermistor to gases and thus reduce the accuracy of the flow rate reading.

In a more preferable embodiment, the flow rate of the gases flow would be determined by supplying current to thermistor 35 to raise its temperature above the temperature of the gases flow by a preselected difference temperature, for example 60° C. Controller 11 then monitors the power drawn by thermistor 35 in maintaining the fixed temperature difference. The power usage in association with the cross-sectional area of the gases flow (for example a 12 mm diameter conduit in the region of the flow probe) provide the controller 11 with an indication of the flow rate, allowing the controller to determine the actual flow rate of the gases. In order for thermistor 35 to maintain the difference temperature it will be necessary to occasionally determine the actual temperature of thermistor 35 while also heating thermistor 35. This may be achieved by removing the heating current from the thermistor temporarily and placing a low sensing voltage across thermistor 35 and sensing the current through thermistor 35. In this way the resistance of thermistor 35 can quickly be measured and a value of temperature deduced from previously stored characteristic temperature versus resistance data for thermistor 35. The sensing voltage may then be removed and the heating current reapplied if the predetermined temperature difference has not been achieved or controller 11 may delay applying further heating to thermistor 35 if the temperature difference has been met or exceeded.

As the exposed surfaces of flow probe 19 will generally be at a lower temperature than the humidified gases flow passing over it, condensation is likely to occur on its surfaces. It should be understood that any liquid water accumulating on the flow sensing thermistor 35 will adversely affect the flow rate reading as the liquid water will absorb some of the heat produced by the thermistor. In order to reduce or eliminate the occurrence of liquid water accumulation on the sensors, the flow probe according to the preferred embodiment of the present invention is provided with at least one "wing" or projecting tab means and in the example shown in FIGS. 1 and 2 two tab means (37, 38, 39 and 40) are shown per sensor housing means (although it may be possible to utilise one projecting tab means per sensor housing means). In cross-section each tab means is preferably rectangular and extends along the length of the sensor housing means from stem 31 to the sensing end of the sensor housing means (although it may not be necessary for the projecting tab means to extend the full length of the sensor housing means). In the preferred embodiment the outer edge of the projecting tab means is substantially a constant distance from the centre line of the sensor housing means along its entire length. As the sensor housing means is tapered, the projecting tab means is therefore triangular in elevation extending preferably perpendicularly from the sensor housing means surface. Preferably the projecting tab means are integrally moulded with the flow probe 19, however, it would be possible to separately manufacture the projecting tab means and attach them to the surface of the sensor housing means.

Figure 3:
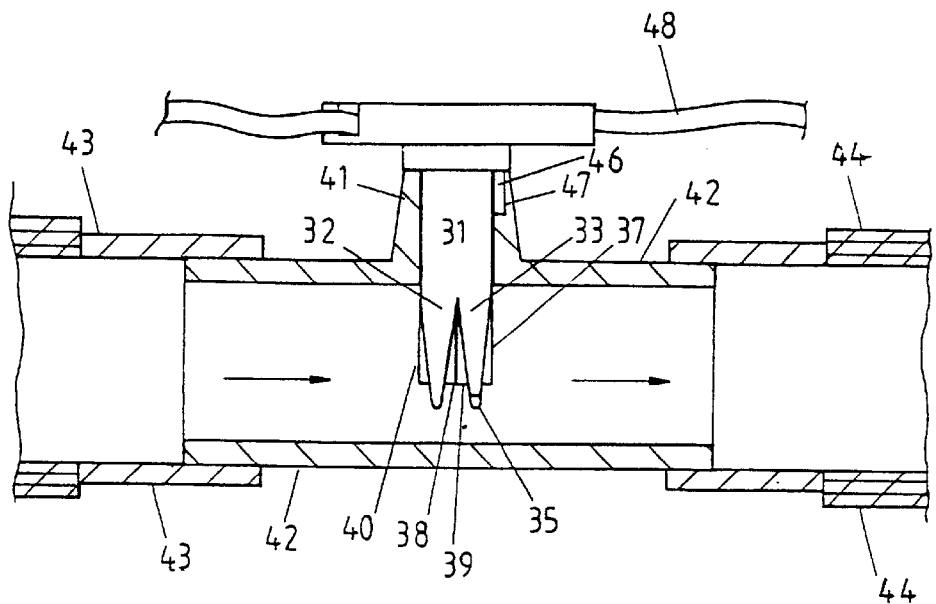
FIG. 3 is a cross-sectional side elevation of a breathing circuit showing the flow probe of FIG. 1 installed within the conduit.
Figure 4:
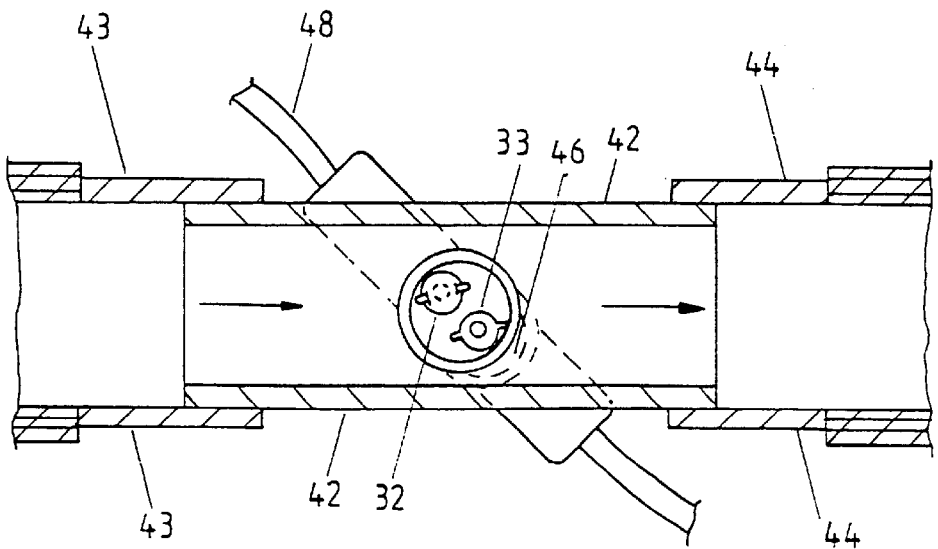
FIG. 4 is a cross-sectional view from below of the breathing circuit of FIG. 3 showing the flow probe of FIG. 1 installed in the conduit.

With reference now also to FIGS. 3 and 4, in use, flow probe 19 is inserted into a sensor entry port 41 in a conduit connector 42. Sensor entry port 41 comprises a substantially cylindrical wall extending perpendicularly from conduit connector 42. Conduit connector 42 connects two conduits 43 and 44 of the breathing circuit or may alternatively be moulded as part of a conduit, for example, as part of inspiratory conduit 14. As may be seen most clearly in FIG. 4, the flow probe 19 is positioned with relation to the gases flow (indicated by arrows) to ensure that the projecting tab means 37, 38, 39 and 40 are each aligned parallel to the gases flow. As condensation forms on the sensor housing means it is caused to run away from the sensor end 36 by the action of the gases flow passing over its surface combined with a localised region of low surface tension in the vicinity of the line of contact of the projecting tab means and the surface of the sensor housing means. Accordingly, condensate tends to flow along the line of intersection (for example line 45) away from sensor end 36 towards stem 31 as desired.

In order to ensure that, upon insertion of flow probe 19 into sensor entry port 41, the projecting tab means are correctly aligned with the gases flow (as incorrect alignment will now produce the desired affect of removing liquid from the sensor tip), the preferred embodiment of the present invention also includes a substantially "V" shaped locating tooth means 46 adjacent the stem 31 and also projecting from base portion 30. A complimentary substantially "V" shaped notch or fixed locating depression 47 is provided in the wall of sensor entry port 41. Accordingly, a user inserting the flow probe 19 will find that in order to fully and securely insert the flow probe into the conduit (or conduit connector), it will be necessary to rotate the flow probe until the locating tooth means 46 and locating depression 47 are combined at which time the flow probe will be correctly aligned to ensure that condensation will tend to run away from the sensor tips as previously described.

Furthermore, in order to ensure that heat generated by the operation of the flow sensing thermistor 35 does not substantially impact upon the temperature sensing thermistor 34, it can be seen in FIG. 4 that upon alignment of locating tooth means 46 and locating depression 47, the temperature and flow sensing thermistors are displaced across the gases flow (that is, they are not aligned in the direction of flow) so that they are each substantially unaffected by the others presence. Also, the heat producing flow sensing thermistor 35 is positioned upstream of the temperature sensing thermistor so that the generated heat is carried away from the temperature sensor by the gases flow.

An advantage of providing a reliable flow probe in the humidification apparatus according to the preferred form of the present invention is that the humidification apparatus can recognise conditions which would impair the humidification apparatus' performance (such as occurrences of suctioning, circuit disconnects and nebulising treatments) by monitoring the flow rate and or temperature for telltale indicative conditions. Once it is determined that a certain recognised condition is occurring, appropriate action may be taken (such as raising an alarm or removing heat from heater plate 9). The humidification apparatus could, for example, determine if the temperature probes have been incorrectly placed or removed from the circuit by, for example sensing no flow with an associated low (ambient) temperature.

The following are a number of preferred uses or applications for the flow probe according to the preferred form of the present invention.

Humidifier Control System—Minimum Power Method

An important parameter of the gases flow supplied to the patient 13 or other person in need of such gases is the humidity. It is well known that gases which are too dry (having a low relative humidity of between around 60% and 70%) can very quickly dehydrate the patient's airways causing discomfort. The controller 11 of the humidification apparatus according to the preferred embodiment of the present invention preferably includes a control system which attempts to maintain the relative humidity of the gases flow at a desirable level (greater than about 90%). One situation where this type of control is desirable is where the temperature of the inlet gases to the humidification chamber 4 rises to a temperature similar to the gases outlet temperature. In this situation, as very little energy is required to be supplied to the gases (to raise their temperature), it is not possible to provide sufficient energy to the water 8 in the humidification chamber and therefore insufficient water vapour is available to humidify to the gases, accordingly, while the temperature of gases supplied to the patient 13 is desirable, the relative humidity is not. When the incoming gases temperature is much less than the required outlet gases temperature then it can virtually be assumed that in the process of providing a large amount of energy in raising the gases temperature to the required value, much water will have been vaporised in the humidification chamber 4 and accordingly the relative humidity of the gases will be high.

Figure 6:
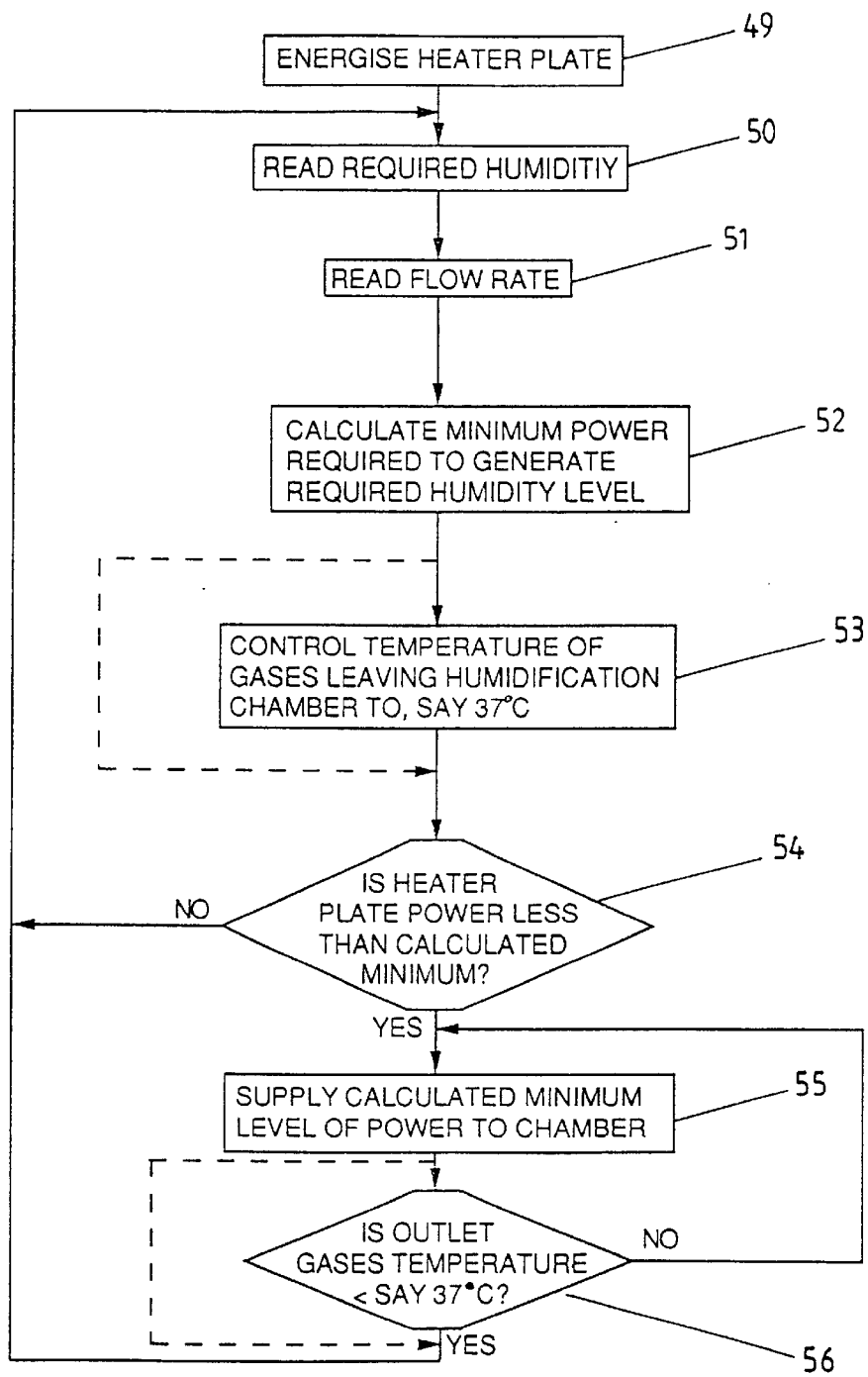
FIG. 6 is a flow diagram of one preferred embodiment of a humidity and temperature control system utilised in the respiratory humidification system shown in FIG. 5.

In order to control the humidity of the gases flow reaching the patient, the humidification apparatus according to the present invention requires information relating to the flow rate of the gases. This may be achieved by inserting a flow probe, preferably as described above, into the gases flow. This control system will now be described with reference to the flow diagram of FIG. 6.

The control system starts at block 49 with heater plate 9 being energised to provide heat to the water within the humidification chamber 4. At block 50 controller 11 reads a required humidity which has either been preset in memory by the manufacturer or has been input by a user via a user input such as user input 20 in FIG. 5. At block 51 controller 11 receives information from flow sensing thermistor 35 in order to determine the flow rate of the gases flow (this may be accomplished as previously described). At block 52 controller 11 determines the minimum power required to generate the required humidity level in the gases flow at the sensed flow rate. This may be achieved by carrying out a calculation using a formula stored in memory or, preferably, a data storage means or memory device associated with the control means 11 has a data look up table of flow rates and their associated minimum required power values at a number of desired humidity levels stored therein which is interrogated by the control means using the sensed flow rate and the required humidity value. Control means 11 could determine the required power level of heater plate 9 by sensing the gases flow rate and receiving a user input desired humidity level and calculating (or alternatively obtaining from a look up table of experimentally derived or previously calculated values) a required evaporation rate to obtain the desired humidity level at that flow rate. Controller 11 could then calculate (or alternatively obtain from a look up table of experimentally derived or previously calculated values) the power required to be supplied by heater plate 9 in order to produce the determined evaporation rate thus ensuring the required humidity level is achieved.

At block 53 (which is not an essential step in the method) the control means 11 controls the temperature of the gases leaving the outlet of the humidification chamber at a preset (either by the user or manufacturer) temperature (for example 37° C.) in the known way by varying the heater plate 9 temperature or power with gases outlet temperature feedback supplied to the controller via temperature sensor 18 (or by the temperature sensing part of flow probe 19).

At block 54, the present power utilisation of the heater plate 9 is determined and a decision is made as to whether the present power utilisation of the heater plate is less than the value calculated at block 52. The present power utilisation could, for example be calculated by the controller 11 sensing the current supplied to the heater plate and multiplying this sensed current value by the voltage supplied to the heater plate. Alternatively, the heater plate average power could be determined by calculating the percentage of time for which the heater plate is energised and multiplying this by the rated power value of the heater plate. For example, if the heater plate is energised for 40% of the time and the rate power of the heater plate is 150 Watts then the average power utilised by the heater plate would be 60 Watts. It could be assumed that the heater plate voltage will be constant. If the presently determined power utilisation is not less than the minimum value determined to be necessary to provide the desired humidity level then control returns to block 50 where the previously described steps are repeated, the patient receiving appropriately humidified gases, until the decision at block 54 reveals that the heater plate power consumption has dropped below the required level to supply adequately humidified gases.

At this point, control passes to block 55 where the power supplied to heater plate 9 is increased (for example by varying a pulse width modulated supply voltage to the heater plate or simply increasing a variable voltage supply) to the level determined in block 52 in order to ensure that the gases are adequately humidified. This will cause the outlet gases temperature to rise above the set temperature, however this is necessary in order to provide adequate humidity. A check is then made at block 56 (which is also not a required step in the method) to see if the outlet gases temperature has dropped below a predetermined temperature (say 37° C.). If the outlet gases temperature has dropped below the predetermined temperature then it can be assumed that the gases will be receiving the required level of humidity as they are at a temperature sufficiently above the assumed gases inlet temperature. If the outlet gases temperature has not dropped to below the predetermined temperature then the calculated minimum power level continues to be supplied to the gases. It can therefore be seen that:

1) in the absence of a temperature sensor, the control system will continually supply to the heater plate the calculated minimum required power to achieve adequate humidification, or 2) where a temperature sensor is supplied, the control system will operate in two modes, a first "normal" mode where the outlet temperature is controlled in the known way to a desired temperature until the power utilisation of the heater plate drops to a level which indicates insufficient humidification at which point a new control mode operates to maintain the heater plate power usage at the calculated minimum level until the outlet gases temperature drops below a preset temperature indicating that the inlet gases temperature has dropped sufficiently to allow the humidification chamber to supply sufficient heat and humidity to the gases flow.

Humidifier Control System—Desired Humidity Method

An alternative humidifier control system to that set out above will now be described with reference to FIG. 7. According to this alternative preferred control system, it is possible to control the humidity of the gases leaving the humidification chamber 4 to any desired level at any gases flow rate. This is made possible by determining the gases flow rate, preferably using the flow probe described above, along with knowledge of the humidification chamber output versus flow and or breathing circuit characteristics.

Figure 7:
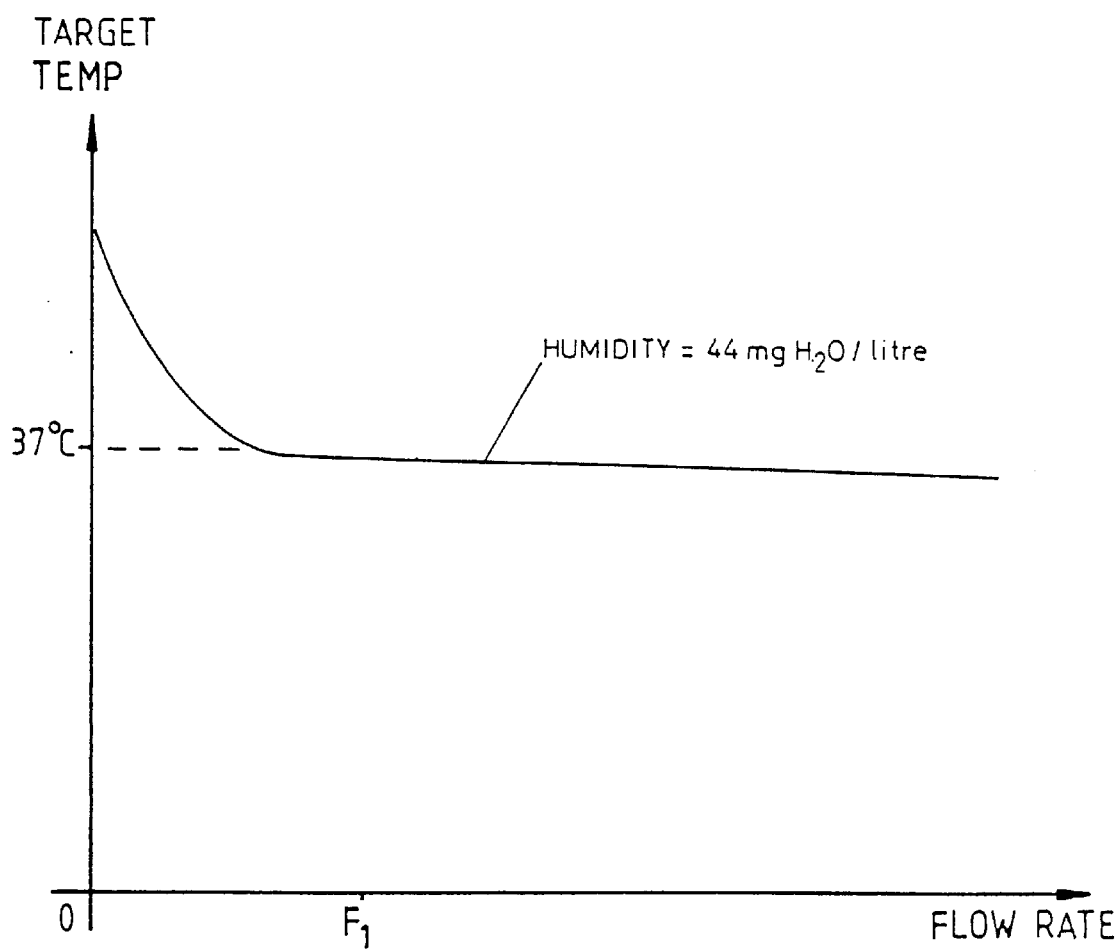
FIG. 7 is a graph of the target outlet temperature required (for a desired humidity level) versus flow rate illustrating one preferred embodiment of a humidity and/or temperature control system utilised in the respiratory humidification system shown in FIG. 5.

An example of the humidification chamber output characteristics are shown in FIG. 7 where it can be seen that for a given required gases humidity level, as gases flow rate is increased, the temperature of the gases at the humidification chamber outlet drops rather steeply and then settles to a substantially constant temperature. This information may be experimentally derived for a number of target gases outlet temperatures and humidity levels and recorded in a memory storage device (for example in the form of a look-up table or a number of look-up tables) searchable by control means 11.

In accordance with this control system, the user enters a desired humidity level to controller 11 by way of a user input device such as user input means 20 which may in this case comprise a dial or electronic key pad. The heater plate 9 is then energised to warm the water within humidification chamber 4 and temperature probe 18 (or the temperature sensing part of flow probe 19) is used to provide a sensed outlet gases temperature signal to control means 11. Utilising the present flow rate value sensed by flow probe 19 and the sensed temperature, controller 11 interrogates its memory device to determine the target outlet gases temperature required to achieve the desired humidity level at the present gases flow rate.

At this point control means 11 controls the energisation of heater plate 9 in order to obtain the determined target outlet gases temperature which will provide the required level of gases humidity at the present gases flow rate. Energisation of heater plate 9 may, for example, take the form of pulse width modulation of the voltage supply to vary the power supplied to the heater plate or alternatively a variable voltage supply could supply the heater plate.

As changes are made in either the flow rate of the gases or in the user set desired humidity level, controller 11 automatically determines an updated target outlet gases temperature from its storage device and appropriately controls heater plate 9 to provide the outlet gases temperature.

For example, for a user set desired humidity level of 44 mg $H_2O$ per liter of gases and a sensed flow rate $F_1$, controller 11 will interrogate the tables in the storage device to determine a target gases outlet temperature of 37° C. is required. Controller 11 then energises heater plate 9 in such a way (for example by PWM control of the supply voltage or current) that the outlet gases temperature sensed by temperature sensor 34 is substantially equal to the target temperature of 37° C. resulting in the desired absolute humidity of 44 mg $H_2O$ per liter.

As an addition to this control system, the memory device associated with control means 11 could also be supplied with information relating to the condensation characteristics of the inspiratory conduit. A heater wire 15 may be energised by control means 11 to control the additional heating to the gases as they pass along the conduit to thereby reduce condensation in the conduit. This also reduces changes in the humidity level of the gases along the conduit (as less water will come out of the gases as condensation). In this control system controller 11 may adjust the heating supplied by heater wire 15 so that as well as controlling humidity of the gases flow the temperature may also be controlled (although in practice the heater wire could only supply a few degrees of temperature increase). However, controller 11 may also conceivably use the heater wire setting to reduce humidity of the gases if they were being supplied at an excess level (in order to produce gases of a sufficiently high temperature) by causing rain-out to occur. Control means 11 would then manipulate the heater plate and heater wire settings appropriately to provide the required gases humidity and temperature (set by a user) to the patient to the best of its ability.

Automated Humidification Apparatus—"Single Button Humidifier"

As a result of implementing either of the above control systems in the humidification apparatus of FIG. 5, it would be possible to provide a humidifier which was extremely simple to use, requiring minimal input from a user. An example of a simple to use humidification apparatus would be as shown in FIG. 5 with the only user input being switch 20. Switch 20 would preferably have a number of states or positions corresponding to a predetermined number of gases delivery configurations. One gases delivery configuration could be Intubated Airways and another could be Intact Airways. For each position or state of switch 20, a corresponding optimally required humidity value and temperature value is stored in a memory associated with controller 11. For example, for the Intubated Airways configuration the optimal temperature may be about 37° C. and the optimal humidity value about 44 mg $H_2O$ per liter of gases while the Intact Airways optimal temperature may be about 32° C. and the optimal humidity value about 30 mg $H_2O$ per liter of gases.

By utilising either one of the above described control systems it would thus be possible to control operation of the humidification apparatus without further user intervention once the gases delivery configuration is known. The controller 11 would repeatedly sense outlet gases temperature and flow rate and adjust heater plate power and possibly heater wire setting to automatically provide optimal (or as near to optimal as possible) gases temperature and humidity to patient 13, independent of changes in flow rate or inlet gases temperature.

User Output—Temperature Display

A further feature of the humidification apparatus according to a further aspect of the present invention is the incorporation of a display means 60 (FIG. 5) for displaying to the user the gases temperature being supplied to the patient 13. It should be noted that this feature does not rely on the presence of a flow probe in the breathing circuit. Display means 60 is controlled by control means 11. It is known that other respiratory humidifiers incorporate display means, however, the temperature which is displayed is invariably fixed at either the temperature of the gases at the patient end of inspiratory conduit 14 (as sensed by temperature sensor 17) or the temperature of the gases at the humidification chamber outlet (as sensed by temperature sensor 18).

Many health care professionals equate the displayed temperature with the amount of moisture contained in the gases. So long as the gases supplied to the patient are at 100% relative humidity (that is, the gases contain as much water vapour as they can possibly hold at their present temperature) then the temperature of the gases supplied to the patient would be clinically accurate. However, if the delivered gases contain less than the maximum possible amount of moisture at their present temperature, then a humidifier which simply displays the delivered gases temperature could mislead a health care professional into believing that the patient is receiving more humidity than they actually are.

In the preferred form of the present invention, the temperature which is displayed on display means 60 is either the temperature sensed by sensor 14 or sensor 18, whichever is the lowest. As an example, a gases outlet temperature of 37° C. and an absolute humidity of 44 mg $H_2O$ per liter of gases (approximately 100% relative humidity) may translate to an inspiratory conduit patient end temperature of 35° C. and an absolute humidity of 35 mg $H_2O$ per liter of gases at the patient. Accordingly 9 mg $H_2O$ per liter of gases is condensing in the inspiratory conduit while the gas remains at approximately 100% relative humidity along the conduit due to the drop in temperature. In this situation, the appropriate temperature to display to the user is 35° C. as a gas at a relative humidity of 100% at this temperature contains the amount of moisture indicated by a temperature of 35° C.

If however the gases outlet temperature was 37° C. with an absolute humidity of 44 mg $H_2O$ per liter of gases (100% relative humidity) and the patient end temperature was 39° C. with an absolute humidity of 44 mg $H_2O$ per liter of gases then the most clinically relevant temperature to display would be 37° C. This is because the gases arriving at the patient will no longer be at 100% relative humidity as no extra moisture has been provided to the gases along the inspiratory conduit although the gases have risen in temperature. This absolute humidity of the gases arriving at the patient is actually associated with a gases temperature of 37° C. as this is the temperature corresponding to the amount of moisture within the humidified gases. In any event, as the patient end temperature is often measured at a distance of up to 30 cm from the patient, by the time the gases arrive at the patient they have often dropped and so the lower temperature of 37° C. is even more relevant to health care professionals.

Automatic No Flow Standby Mode

As has previously been mentioned, in many existing humidification systems, the controller simply senses temperature in order to adjust power delivered by the humidifier heater plate 9 and/or conduit heater wire 15. In a situation where the gases supply means or blower 1 is disconnected from the breathing circuit these types of controllers will sense a lack of temperature as there will be no gases flow passing the temperature sensor. The controller then attempts to increase the temperature of the gases (which it assumes are still flowing in the breathing circuit) by increasing the power supplied to heater plate 9 and/or heater wire 15. As the temperature sensors are not able to register any increase in temperature of the "flow", the controller 11 may continue to increase the power supplied to heating the non-existent gases flow to a dangerous level. If the gases supply is then re-established, the gases supplied to the patient could be at an unsafe temperature.

In order to avoid the above series of events occurring, the flow sensor according to the preferred form of the present invention could be incorporated into a humidification system. The controller could then determine if the humidifier has sufficient gases flow (say, for example 1.5 liters per minute) for normal safe operation. If the gases flow is found to be insufficient then the humidifier could be placed into a safe mode of operation. The safe mode could include a limit on heater plate 9 temperature and/or limits on the duty cycle of voltage supplied to heater plate 9 and/or heater wire 15 (that is, control of power levels).

Humidity Alarm

It is believed that an alarm (such as an audible and/or visual alarm) should be provided in a humidification system to warn the patient (or health care professional) when the gases supplied to the patient have been below (or above) the required humidity level for a period of time. It has been found that the alarm should be set to go off after a period of time which is dependent on the difference between the required humidity and the actual humidity level being supplied to the patient. The larger the difference, the sooner the alarm should occur.

Figure 8:
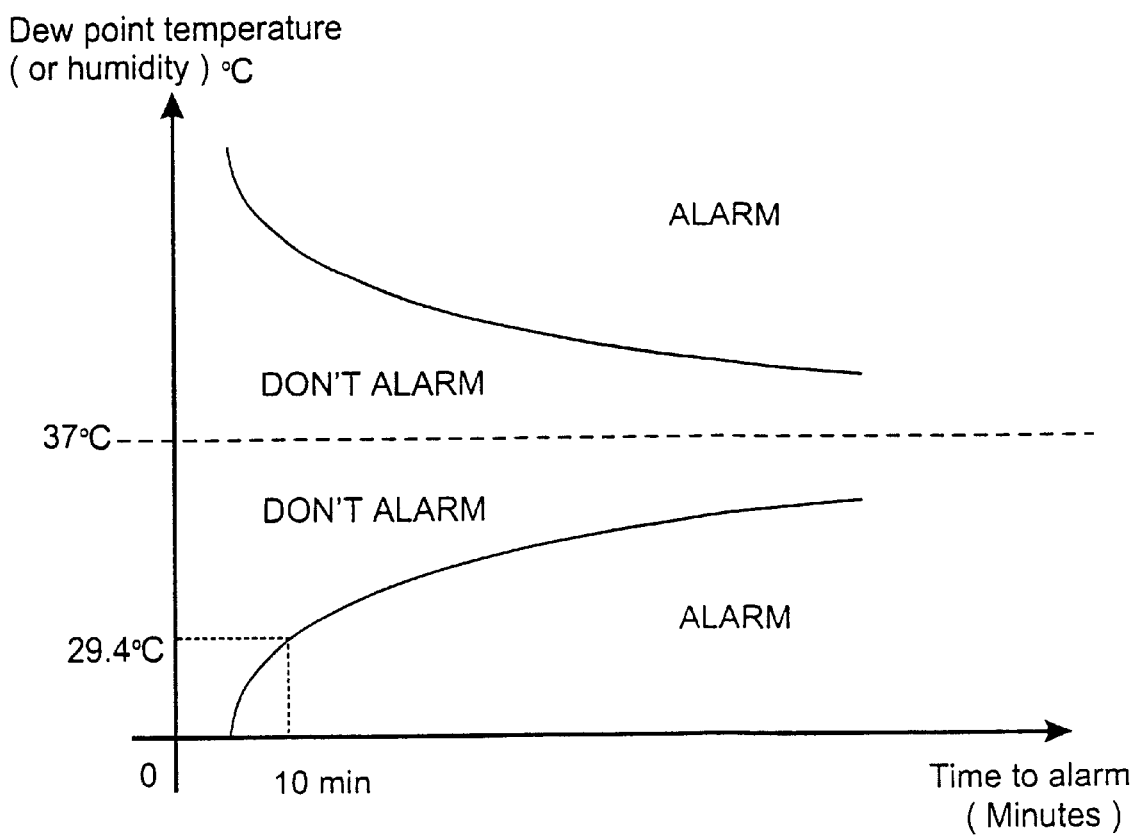
FIG. 8 is a graph of humidity (or dewpoint) versus time to alarm in an example humidification system such as that shown in FIG. 5.

FIG. 8 shows one possible graphical example of how the time delay may be set, based on the patient's physiological humidity needs. A number of different such "humidity profiles" could be stored in a memory device, each one based around a predetermined required humidity value (the example shows a required humidity value of 37° C.). The relationship between temperature difference and time to alarm could conveniently be expressed in a table format stored in, for example, ROM (Read Only Memory) to be read by control means 11 such that the control means determines the humidity difference, looks up that difference in a table (the table selected depending on the required humidity value) which provides the appropriate time to wait before issuing the alarm. An alternative to measuring the humidity of the gases supplied is to monitor the actual dew point (temperature at which condensation starts to occur) of the gases and to determine the difference between the actual dewpoint and the required or optimal dewpoint (for example 37° C.). The actual dew point could, for example be assumed to be the lower of the humidification chamber 4 temperature and the conduit 14 temperature.

Water Out Alarm

In a respiratory humidification system incorporating a humidification chamber 4, it is imperative that a certain minimum level of water is maintained in order for the humidifier to have the ability to supply water vapour to the gases supply. Accordingly, the health care professional administering humidified gases to the patient should occasionally check the water level and add more water when required. This job is sometimes overlooked.

It is possible to utilise flow probe 19 in a humidification system which automatically determines when the water level drops to an insufficient level and raises an alarm. Preferably, the heater plate 9 temperature, the humidification chamber 4 temperature (or chamber outlet temperature) and heater plate 9 power requirement (the amount of power presently being supplied to the heater plate) are all monitored and utilised in the following equation to provide a value for Thermal Conductivity.

$$\text{Thermal Conductivity} = \frac{\text{Heater Plate Power Requirement}}{\text{Heater Plate Temperature} - \text{Chamber Temperature}}$$

Controller 11 compares the calculated thermal conductivity value to a predetermined threshold value (which itself is dependent on the gases flow rate determined by flow probe 19) which may be experimentally determined at various gases flow rates. The calculated Thermal Conductivity value could for example, be updated every 5 minutes for example and an alarm could, for example, be raised after a period of 5 or 10 minutes have elapsed from the calculated Thermal Conductivity value dropping below the threshold (alternatively the alarm could be issued immediately). The following are experimentally determined examples of Thermal Conductivity values and preferred example threshold values at different flow rates:

Flow rate=10 liters/minute
    Thermal Conductivity=1.26 W/°C. (with sufficient water in chamber 4)
    Thermal Conductivity=0.26 W/°C. (without water in chamber 4)
    Predetermined threshold=0.5 W/°C.

Flow Rate=40 liters/minute
    Thermal Conductivity=1.81 W/°C. (with sufficient water in chamber 4)
    Thermal Conductivity=0.42 W/°C. (without water in chamber 4)
    Predetermined threshold=0.8 W/°C.

The predetermined threshold values at a number of flow rates could be stored in ROM accessible by controller 11 so that the controller would simply determine the present flow rate of the gases, calculate the value of Thermal Conductivity, access the table in ROM based on the present flow rate and read out the associated predetermined threshold value. If the calculated threshold value is greater than the calculated Thermal Conductivity value then controller 11 would wait the predetermined period of time (for example, 5 or 10 minutes) before issuing an alarm so that the water level could then be topped up without a loss of humidity in the gases being delivered to the patient.

Chamber Set-Point Tracking

In a respiratory humidification system including a conduit heater wire, temperature and humidity are usually controlled so that gases supplied to the patient arrive at required temperature and humidity levels. In some situations the conduit heater wire 15 supplies sufficient energy to raise the temperature of the gases in the breathing circuit to achieve the desired temperature at the patient. On some occasions, the limited power available from the conduit heater wire (even at 100% duty cycle) is insufficient to raise the gases temperature to the required temperature of gases of the patient. More particularly, the inability of these humidification systems to maintain the required gases temperature at the patient end of conduit 14 usually results in condensation or "rain-out" occurring in the conduit due to the humidified gases giving up too much of their heat to the conduit walls. The controller according to a further preferred embodiment of the present invention includes a system to minimise or alleviate the above problem.

Accordingly, rather than attempting to maintain the patient gases temperature at a desired level, the respiratory humidification system according to a preferred form of the present invention attempts to maintain a "temperature gradient" along the length of conduit 14 and adjusts the required patient temperature (or "Airway set-point") accordingly. The Airway set-point value is calculated as follows:

Airway set-point=chamber outlet temperature+offset

Where the value of "offset" is for example 3° C. and equates to the desired temperature gradient required along the conduit 14. It should be noted that the value of "offset" chosen is dependent on the physical properties and configuration of the conduit.

For example, for an offset of 3° C. and a humidification chamber 4 outlet gases temperature of 37° C., the heater wire 15 will be energised appropriately (for example by adjusting its duty cycle) to maintain the temperature of gases supplied to the patient at 40° C. Similarly, fi the chamber outlet temperature dropped to 31° C. then the temperature of gases supplied to the patient would be controlled to arrive at 34° C. In both instances, a temperature gradient or difference of +3° C. is maintained along the conduit minimising or eliminating condensation.

If it is found that the required offset value is not maintainable (that is, the heater wire is incapable of raising the temperature of the gases in the conduit to the calculated required value sensed by, for example a temperature sensor near the patient end of conduit 14) then controller 11 will decrease the humidification chamber outlet temperature (by for example, reducing the duty cycle of power supplied to heater plate 9) in order to maintain the required offset temperature along the conduit. As an example, the controller could be programmed to begin to drop the humidification chamber outlet temperature in 0.5° C. steps (to a minimum of for example 35.5° C.) if the offset temperature value is not maintainable at at least 2° C. for 15 minutes. For example, for an offset value of 3° C. and an initial chamber outlet temperature of 37° C., the gases supplied to the patient should be controlled to arrive at 40° C. If however the gases arriving at the patient are at 38.6° C. (an actual offset or difference of only 1.6° C.), then controller 11 will drop the humidification chamber outlet temperature to 36.5° C. for 15 minutes. The above calculations will then be repeated and if the temperature of gases reaching the patient is not maintainable at 39.5° C. then controller 11 will again consider dropping the humidification chamber temperature. This process will be repeated until a humidification chamber outlet temperature is reached at which the required conduit offset temperature can be maintained. Furthermore, the controller 11 could then attempt to raise the humidification chamber outlet gases temperature so that the gases supplied to the patient can again be established at a required temperature but only if this can be accomplished under the offset temperature constraint. This would only be possible if ambient circumstances had changed.

Thus, at least in the preferred form, the present invention incorporating all or some of the above described features provides a respiratory humidification system which enables humidity and/or temperature control of the humidified gases to be achieved. The gases flow probed according to one embodiment of the present invention enables accurate flow rate measurements to be made without condensation affecting the sensor. In part this increased accuracy is also due to the locating system which ensures correct alignment of the flow and/or temperature probe in the gases flow. Due to the ability to accurately sense flow rate with this flow sensor, the control systems according to the present invention are able to provide a gases flow to the patient which is controlled to a required humidity. The flow rate sensor also enables "automatic" control to be achieved whereby the user is not required to constantly monitor the output of the humidifier and to alter inputs to achieve desired changes, the user is merely required to inform the humidifier of the patient's gases delivery situation and the humidifier is able to provide the required gases temperature and humidity without further user input. The humidifier also displays a gases temperature value which is clinically relevant to the gases reaching the patient. In addition, the respiratory humidification according to other preferred embodiments of the present invention encompasses various safety improvements over the prior art.

What is claimed is:

1. Sensor probe means adapted for positioning in a flow of humidified gases comprising:

sensor housing means adapted for positioning in said gases flow, said sensor housing means having a longitudinal axis substantially perpendicular to said humidified gases flow and a sensing end, sensing means housed within said sensor housing means at or near said sensing end, and at least one projecting tab means extending laterally from said sensor housing means, said at least one projecting tab means providing surfaces which enable liquid condensate to disperse away from said sensing end of said sensor housing means.

2. Sensor probe means as claimed in claim 1 wherein said sensor probe means comprise two said projecting tab means.

3. Sensor probe means as claimed in claim 1 or claim 2 wherein said two projecting tab means are oppositely positioned around said sensor housing means.

4. Sensor probe means as claimed in claim 1 or claim 2 wherein each said at least one projecting tab means is aligned parallel to said gases flow.

5. Sensor probe means as claimed in claim 1 or claim 2 wherein liquid condensate is dispersed along the lines of intersection between said sensor housing means and said at least one tab means, there existing a localised area of low surface tension along said lines of intersection.

6. Sensor probe means as claimed in claim 1 or claim 2 wherein said sensor probe means comprise two sensor housing means, a temperature sensor housing means and a flow rate sensor housing means.

7. Sensor probe means as claimed in claim 6 wherein said sensing means of said temperature sensor housing means and said flow rate sensor housing means each comprise a temperature dependent resistance.

8. Sensor probe means as claimed in claim 6 wherein said sensing means of said flow rate sensor housing means is occasionally heated to a predetermined difference temperature above the temperature of said gases flow, and the power required by said sensor means of said flow rate sensor housing means to maintain said predetermined difference temperature providing an indication of the flow rate of said gases.

9. Sensor probe means as claimed in claim 6 wherein said sensing means of said flow rate sensor housing means is exposed at or near the sensing end of the flow rate sensor housing means while the sensing means of said temperature sensor housing means is encapsulated at or near the sending end of the temperature sensor housing means.

10. Sensor probe means as claimed in claim 6 wherein said temperature and flow rate sensor housing means are spaced across said gases flow in order that heat produced by the sensing means of said flow rate sensor housing means has substantially minimal effect on the sensing means of said temperature sensor housing means.

11. Sensor probe means as claimed in claim 6 wherein said flow rate sensor housing means is positioned up stream of said temperature sensor housing means in order that heat produced by the sensing means of said flow rate sensor housing means does not effect the sensing means of said temperature sensor housing means.

12. Sensor probe means as claimed in claim 1 or claim 2 wherein said gases flow is channelled within a conduit of known cross-sectional area, at least in the region adjacent said sensor probe means, and is provided with a sensor entry port adapted to receive said sensor probe means, said sensor entry port being provided with a fixed locating depression and said senor probe means being provided with a complimentary fixed locating tooth, the positioning of said temperature and flow rate sensor housing means relative to said gases flow being controlled by the interconnection of said locating depression and tooth.

* * * * *

UNITED STATES PATENT AND TRADEMARK OFFICE
CERTIFICATE OF CORRECTION

PATENT NO.   : 6,272,933 B1
DATED        : August 14, 2001
INVENTOR(S)  : Lewis George Gradon et al.

It is certified that error appears in the above-identified patent and that said Letters Patent is hereby corrected as shown below:

Column 15,
Line 50, "This" should read -- The --

Column 18,
Line 16, "fi" should read -- if --

Column 20,
Line 37, "senor" should read -- sensor --

Signed and Sealed this

Ninth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,272,933 B1
DATED          : August 14, 2001
INVENTOR(S)    : Lewis George Gradon et al.

It is certified that error appears in the above-identified patent and that said Letters Patent is hereby corrected as shown below:

Title page,
Insert Item -- [30] Foreign Application Priority Data
June 17, 1997  (NZ) ..........328116
April 27, 1998 (NZ) ..........330295 --

Signed and Sealed this

Twenty-seventh Day of July, 2004

JON W. DUDAS
*Acting Director of the United States Patent and Trademark Office*